(12) United States Patent
Rosati

(10) Patent No.: US 6,821,989 B2
(45) Date of Patent: Nov. 23, 2004

(54) METHOD OF TREATING CERTAIN CANCERS USING AN ESTROGEN AGONIST/ANTAGONIST

(75) Inventor: Robert L. Rosati, Mystic, CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 10/056,397

(22) Filed: Jan. 23, 2002

(65) Prior Publication Data

US 2003/0130276 A1 Jul. 10, 2003

Related U.S. Application Data

(60) Provisional application No. 60/264,566, filed on Jan. 26, 2001.

(51) Int. Cl.[7] ............................................. A61K 31/445
(52) U.S. Cl. ........................ 514/317; 514/331; 514/427; 514/428
(58) Field of Search ................................. 514/317, 331, 514/427, 428

(56) References Cited

U.S. PATENT DOCUMENTS

| | | | |
|---|---|---|---|
| 4,418,068 A | 11/1983 | Jones | 424/267 |
| 4,623,660 A | 11/1986 | Richardson | 514/514 |
| 4,696,949 A | 9/1987 | Toivola et al. | 514/648 |
| 5,026,707 A | 6/1991 | Nixon et al. | 514/255 |
| 5,192,525 A | 3/1993 | Yang et al. | 424/1.1 |
| 5,552,412 A | 9/1996 | Cameron et al. | 514/317 |
| 5,558,877 A | 9/1996 | Matlin et al. | 424/432 |
| 5,844,001 A | 12/1998 | McClay et al. | 514/648 |
| 5,889,042 A | 3/1999 | MacLean et al. | 514/127 |
| 5,948,809 A | 9/1999 | Chiu et al. | 514/428 |
| 6,107,331 A | 8/2000 | MacLean et al. | 514/428 |
| 6,153,622 A | 11/2000 | Cameron et al. | 514/307 |
| 6,204,286 B1 | 3/2001 | Cameron et al. | 514/428 |
| 6,455,572 B1 * | 9/2002 | Day et al. | 514/424 |

FOREIGN PATENT DOCUMENTS

| | | | |
|---|---|---|---|
| EP | 0702962 | 3/1996 | A61K/45/06 |
| EP | 0729755 | 9/1996 | A61K/31/40 |
| EP | 0843999 | 5/1998 | A61K/31/135 |
| EP | 1004306 | 5/2000 | A61K/31/445 |
| EP | 1118323 | 7/2001 | A61K/31/138 |
| EP | 1120114 | 8/2001 | A61K/31/138 |
| EP | 1177787 | 2/2002 | A61K/31/00 |
| WO | WO 9640616 | 12/1996 | C07C/211/00 |
| WO | WO 9726878 | 7/1997 | A61K/31/44 |
| WO | WO 9856387 | 12/1998 | A61K/31/59 |

OTHER PUBLICATIONS

Stein, J. H., Editor–in–Chief, Internal Medicine, 4th Edition, Chapters 71 and 72, 1994.*
U.S. non–provisional application No. 09/758778, filed Jan. 11, 2001 (our docket No. PC10629ATMC).
U.S. non–provisional application No. 09/757423, filed Jan. 10, 2001 (our docket No. PC10631ATMC).
U.S. non–provisional application No. 09/767625, filed Jan. 23, 2001 (our docket No. PC10633ATMC).
U.S. non–provisional application No. 09/757817, filed Jan. 10, 2001 (our docket No. PC10640ATMC).
Yang, et al., Organic Letters, "Enzyme–Catalyzed Asymmetric Deacylation for the Preparation of Lasofoxifene (CP–336156), a Selective Estrogen Receptor Modulator", vol. 2, No. 25, pp. 4025–4027, (2000).
Edward P. Gelman, Seminars in Oncology, "Tamoxifen for the Treatment of Malignancies Other Than Breast and Endometrial Carcinoma", vol. 24, No. 1, Suppl. 1, pp. 65–70, (Feb. 1997).
Rosati, et al., J. Med. Chem, "Discovery and Preclinical Pharmacology of a Novel, Potent, Nonsteroidal Estrogen Receptor Agonist/Antagonist, CP–336156, a Diaryltetrahydronaphthalene", vol. 41, pp. 2928–2931, (1998).
Johnson et al, Proceedings: The 45th ASMS Conference on Mass Spectrometry and Applied Topics, Jun. 1–5, 1997, Palm Springs, CA.
Johnson et al, Proceedings: The 46th ASMS Conference on Mass Spectrometry and Applied Topics, May 31–Jun. 4, 1998, Orlando, FL.

* cited by examiner

*Primary Examiner*—Dwayne Jones
(74) *Attorney, Agent, or Firm*—Peter C. Richardson; Gregg C. Benson; John A. Wichtowski

(57) ABSTRACT

The present invention provides methods of treating cancer of the liver, ovarian cancer, a desmoid tumor, glioma, pancreatic cancer, or renal cell carcinoma using an estrogen agonist/antagonist. The present invention also provides kits that contain an estrogen agonist/antagonist for treating cancer of the liver, ovarian cancer, a desmoid tumor, glioma, pancreatic cancer, or renal cell carcinoma.

9 Claims, No Drawings

METHOD OF TREATING CERTAIN CANCERS USING AN ESTROGEN AGONIST/ANTAGONIST

CROSS REFERENCE TO RELATED APPLICATION

This application claims priority from of U.S. provisional application No. 60/264,566, filed Jan. 26, 2001.

FIELD OF THE INVENTION

The present invention provides methods of treating cancer of the liver, ovarian cancer, a desmoid tumor, glioma, pancreatic cancer, or renal cell carcinoma that comprise administering to a patient having cancer of the liver, ovarian cancer, a desmoid tumor, glioma, pancreatic cancer, or renal cell carcinoma a therapeutically effective amount of an estrogen agonist/antagonist. The present invention also provides kits for treating cancer of the liver, ovarian cancer, a desmoid tumor, glioma, pancreatic cancer, or renal cell carcinoma that comprises a pharmaceutical composition comprising an estrogen agonist/antagonist and instructions for administering the pharmaceutical composition to treat cancer of the liver, ovarian cancer, a desmoid tumor, glioma, pancreatic cancer, or renal cell carcinoma.

BACKGROUND OF THE INVENTION

Cancer is still one of the most dreaded diseases, and much effort and money has been spent trying to discover ways to treat cancer. The present invention provides methods of treating certain cancers, namely cancer of the liver, ovarian cancer, a desmoid tumor, glioma, pancreatic cancer, or renal cell carcinoma.

There are two main types of cancer of the liver. The first type is the result of metastasis of cancer from another area in the body. In this type of liver cancer, a cancer cell from another part of the body migrates to the liver and begins growth and tumor formation there. Commonly, the cancer cells that metastasize to the liver come from cancer in the lungs, breast, colon, pancreas or stomach.

The second general type of liver cancer has been called primary liver cancer. This type is composed of subtypes of cancers such as hepatocelluar carcinoma, which is the most common type of liver cancer, fibrolamellar carcinoma, cholangiocarcinoma, hepatoblastoma and angiosarcoma.

Ovarvian cancer is the second most commonly diagnosed and most deadly gynecologic malignancy. Ovarian cancer affects predominantly perimenopausal and postmenopausal women.

Desmoid tumors, also called aggressive fibromatosis, are dense connective tissue tumors.

Glioma is a type of brain tumor, which accounts for 45% of intracranial tumors.

Pancreatic cancer has several varieties including ductal adenocarcinoma, cystadenocarcinoma, intraductal papillary-mucinous tumors, insulinoma, Zollinger-Ellison Syndrome (also known as gastrinoma), vipoma and glucagonoma.

Renal cell carcinoma accounts for about two percent of cancers.

The cancers listed above can all be treated by administering to a patient suffering therefrom a therapeutically effective amount of an estrogen agonist/antagonist.

The use of tamoxifen to treat ovarian cancer, heptaocellular carcinoma, desmoid tumors, malignant gliomas, carcinoma of the pancreas and melanoma is discussed in Gelman, Edward P., *Tamoxifen for the Treatment of Malignancies Other Than Breast and Endometrial Carcinoma, Seminars in Oncology*, Vol. 24, No. 1, Suppl I (February), 1997, pp SI-65-SI 70.

SUMMARY OF THE INVENTION

The present invention provides methods of treating cancer of the liver, ovarian cancer, a desmoid tumor, glioma, pancreatic cancer, or renal cell carcinoma, the methods comprising the step of administering to a patient having cancer of the liver, ovarian cancer, a desmoid tumor, glioma, pancreatic cancer, or renal cell carcinoma a therapeutically effective amount of an estrogen agonist/antagonist.

In a preferred embodiment of the methods, the estrogen agonist/antagonist is a compound of formula (I):

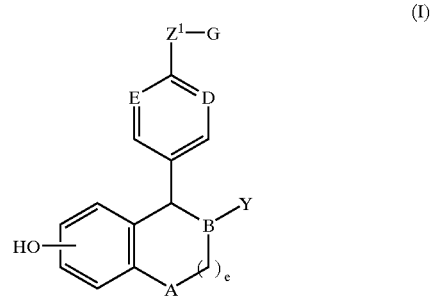

wherein:

A is selected from $CH_2$ and NR;

B, D and E are independently selected from CH and N;

Y is
 (a) phenyl, optionally substituted with 1–3 substituents independently selected from $R^4$;
 (b) naphthyl, optionally substituted with 1–3 substituents independently selected from $R^4$;
 (c) $C_3$–$C_8$ cycloalkyl, optionally substituted with 1–2 substituents independently selected from $R^4$;
 (d) $C_3$–$C_8$ cycloalkenyl, optionally substituted with 1–2 substituents independently selected from $R^4$;
 (e) a five membered heterocycle containing up to two heteroatoms selected from the group consisting of —O—, —$NR^2$— and —$S(O)_n$—, optionally substituted with 1–3 substituents independently selected from $R^4$;
 (f) a six membered heterocycle containing up to two heteroatoms selected from the group consisting of —O—, —$NR^2$— and —$S(O)_n$— optionally substituted with 1–3 substituents independently selected from $R^4$; or
 (g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;

$Z^1$ is
 (a) —$(CH_2)_p$ $W(CH_2)_q$—;
 (b) —$O(CH_2)_p$ $CR^5R^6$—;
 (c) —$O(CH_2)_p W(CH_2)_q$—;
 (d) —$OCHR^2CHR^3$—; or
 (e) —$SCHR^2CHR^3$—;

G is
(a) —NR⁷R⁸;

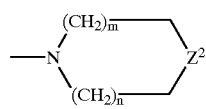
(b)

wherein n is 0, 1 or 2; m is 1, 2 or 3; $Z^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from $R^4$; or (c) a bicyclic amine containing five to twelve carbon atoms, either bridged or fused and optionally substituted with 1–3 substituents independently selected from $R^4$; or $Z^1$ and G in combination may be

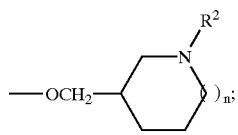

W is
(a) —CH$_2$—;
(b) —CH=CH—;
(c) —O—;
(d) —NR$^2$—;
(e) —S(O)$_n$—;

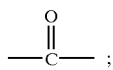
(f)

(g) —CR$^2$(OH)—;
(h) —CONR$^2$—;
(i) —NR$^2$CO—;

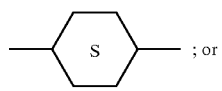
(j)

(k) —C≡C—;
R is hydrogen or C$_1$–C$_6$ alkyl;
$R^2$ and $R^3$ are independently
  (a) hydrogen; or
  (b) C$_1$–C$_4$ alkyl;
$R^4$ is
  (a) hydrogen;
  (b) halogen;
  (c) C$_1$–C$_6$ alkyl;
  (d) C$_1$–C$_4$ alkoxy;
  (e) C$_1$–C$_4$ acyloxy;
  (f) C$_1$–C$_4$ alkylthio;
  (g) C$_1$–C$_4$ alkylsulfinyl;
  (h) C$_1$–C$_4$ alkylsulfonyl;
  (i) hydroxy (C$_1$–C$_4$)alkyl;
  (j) aryl (C$_1$–C$_4$)alkyl;
  (k) —CO$_2$H;
  (l) —CN;
  (m) —CONHOR;
  (n) —SO$_2$NHR;
  (o) —NH$_2$;
  (p) C$_1$–C$_4$ alkylamino;
  (q) C$_1$–C$_4$ dialkylamino;
  (r) —NHSO$_2$R;
  (s) —NO$_2$;
  (t) -aryl; or
  (u) —OH;
$R^5$ and $R^6$ are independently C$_1$–C$_8$ alkyl or together form a C$_3$–C$_{10}$ carbocyclic ring;
$R^7$ and $R^8$ are independently
  (a) phenyl;
  (b) a C$_3$–C$_{10}$ carbocyclic ring, saturated or unsaturated;
  (c) a C$_3$–C$_{10}$ heterocyclic ring containing up to two heteroatoms, selected from —O—, —N— and —S—;
  (d) H;
  (e) C$_1$–C$_6$ alkyl; or
  (f) form a 3 to 8 membered nitrogen containing ring with $R^5$ or $R^6$;
$R^7$ and $R^8$ in either linear or ring form may optionally be substituted with up to three substituents independently selected from C$_1$–C$_6$ alkyl, halogen, alkoxy, hydroxy and carboxy;
a ring formed by $R^7$ and $R^8$ may be optionally fused to a phenyl ring;
e is 0, 1 or 2;
m is 1, 2 or 3;
n is 0, 1 or 2;
p is 0, 1, 2 or 3;
q is 0, 1, 2 or 3;
or an optical or geometric isomer thereof; or a pharmaceutically acceptable salt, N-oxide, ester, quaternary ammonium salt or prodrug thereof.

In another preferred embodiment of the methods, the estrogen agonist/antagonist is a compound of formula (IA)

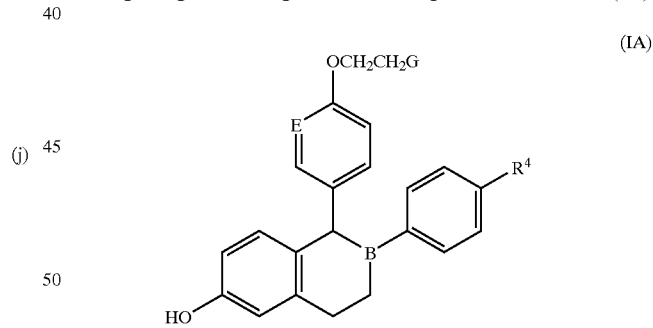
(IA)

wherein G is

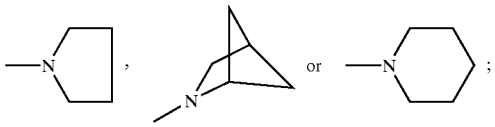

$R^4$ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

In another preferred embodiment of the methods, the estrogen agonist/antagonist is (−)-cis-6-phenyl-5-[4-(2- pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof.

In another preferred embodiment of the methods, the estrogen agonist/antagonist is (−)-cis-6-phenyl-5-[4-(2-pyrrolidin-1-yl-ethoxy)-phenyl]-5,6,7,8-tetrahydro-naphthalene-2-ol, D-tartrate salt.

In another preferred embodiment of the methods, the estrogen agonist/antagonist is 4-hydroxy tamoxifen, droloxifene, toremifene, centchroman, idoxifene, raloxifene, 6-(4-hydroxy-phenyl)-5-[4-(2-piperidin-1-yl-ethoxy)-benzyl]-naphthalen-2-ol, {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone, EM-652, EM-800, GW 5638, GW 7604, or an optical or geometric isomer thereof; pharmaceutically acceptable salt, N-oxide, ester, quaternary ammonium salt, or prodrug thereof.

In another preferred embodiment of the methods, the estrogen agonist/antagonist is a compound of formula V or VI:

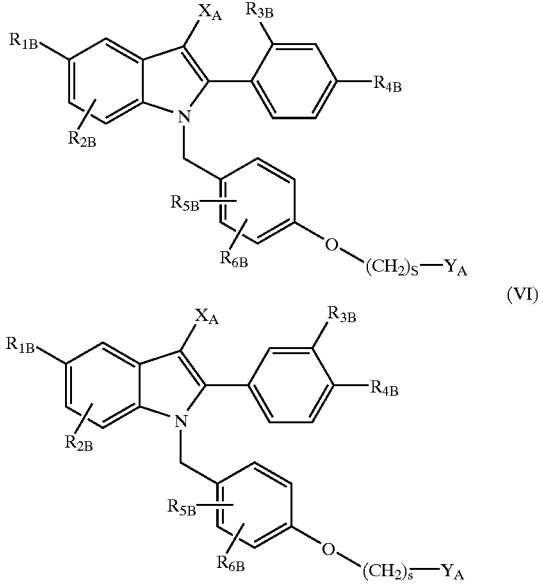

wherein:

$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or $C_1$–$C_4$ halogenated ethers;

$R_{2B}$, $R_{3B}$, $R_{4B}$, $R_{5B}$, and $R_{6B}$ are independently selected from H, OH, —O—C(O)—$C_1$–$C_{12}$ (straight chain or branched), —O—$C_1$–$C_{12}$ (straight chain or branched or cyclic), halogens, or $C_1$–$C_4$ halogenated ethers, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$ is the moiety:

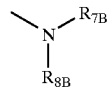

wherein:
a) $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$; or b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$alkyl)$_2$, —$NHSO_2R_{1B}$, —$NHCOR_{1B}$, —$NO_2$, or phenyl optionally substituted with 1–3 ($C_1$–$C_4$)alkyl; or f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$) alkyl; or an optical or geometric isomer thereof; or a pharmaceutically acceptable salt, N-oxide, ester, quaternary ammonium salt or prodrug thereof.

In another preferred embodiment of the methods, the estrogen agonist/antagonist is the compound of formula Va:

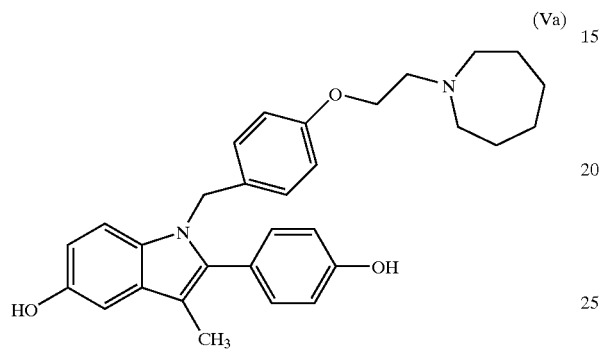

(Va)

or an optical or geometric isomer thereof; or a pharmaceutically acceptable salt, N-oxide, ester, quaternary ammonium salt or prodrug thereof.

In another preferred embodiment of the methods, the estrogen agonist/antagonist is the compound of formula III (EM-652) or formula IV (EM-800) below:

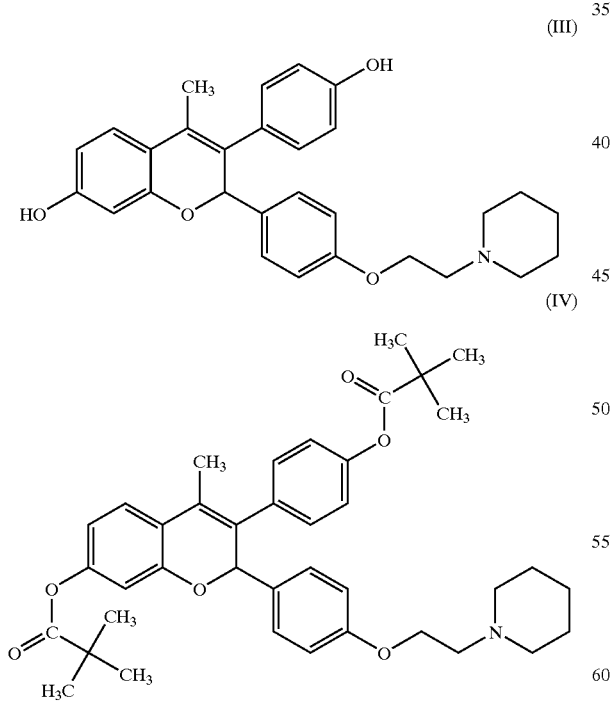

(III)

(IV)

or an optical or geometric isomer thereof; or a pharmaceutically acceptable salt, N-oxide, ester, quaternary ammonium salt or prodrug thereof.

Also provided by the present invention are kits for use by a consumer to treat cancer of the liver, ovarian cancer, a desmoid tumor, glioma, pancreatic cancer, or renal cell carcinoma, the kits comprising:

(a) a pharmaceutical composition comprising an estrogen agonist/antagonist; and (b) instructions describing a method of using the pharmaceutical composition to treat cancer of the liver, ovarian cancer, a desmoid tumor, glioma, pancreatic cancer, or renal cell carcinoma.

In a preferred embodiment of the kits, the estrogen agonist/antagonist is a compound of formula (I):

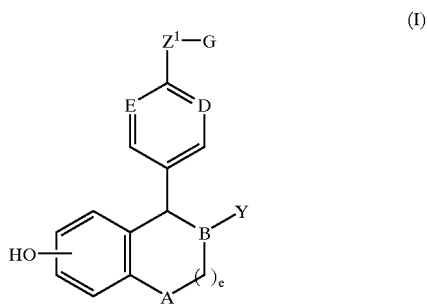

(I)

wherein:

A is selected from $CH_2$ and NR;

B, D and E are independently selected from CH and N;

Y is (a) phenyl, optionally substituted with 1–3 substituents independently selected from $R^4$;

(b) naphthyl, optionally substituted with 1–3 substituents independently selected from $R^4$;

(c) $C_3$–$C_8$ cycloalkyl, optionally substituted with 1–2 substituents independently selected from $R^4$;

(d) $C_3$–$C_8$ cycloalkenyl, optionally substituted with 1–2 substituents independently selected from $R^4$;

(e) a five membered heterocycle containing up to two heteroatoms selected from the group consisting of —O—, —$NR^2$— and —$S(O)_n$—, optionally substituted with 1–3 substituents independently selected from $R^4$;

(f) a six membered heterocycle containing up to two heteroatoms selected from the group consisting of —O—, —$NR^2$— and —$S(O)_n$— optionally substituted with 1–3 substituents independently selected from $R^4$; or (g) a bicyclic ring system consisting of a five or six membered heterocyclic ring fused to a phenyl ring, said heterocyclic ring containing up to two heteroatoms selected from the group consisting of —O—, —$NR^2$— and —$S(O)_n$—, optionally substituted with 1–3 substituents independently selected from $R^4$;

$Z^1$ is (a) —$(CH_2)_p W(CH_2)_q$—;

(b) —$O(CH_2)_p CR^5R^6$—;

(c) —$O(CH_2)_p W(CH_2)_q$—;

(d) —$OCHR^2CHR^3$—; or (e) —$SCHR^2CHR^3$—;

G is
(a) —NR⁷R⁸;

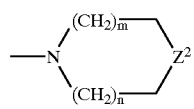
(b)

wherein n is 0, 1 or 2; m is 1, 2 or 3; Z² is —NH—, —O—, —S—, or —CH₂—; optionally fused on adjacent carbon atoms with one or two phenyl rings and, optionally independently substituted on carbon with one to three substituents and, optionally, independently on nitrogen with a chemically suitable substituent selected from R⁴; or (c) a bicyclic amine containing five to twelve carbon atoms, either bridged or fused and optionally substituted with 1–3 substituents independently selected from R⁴; or Z¹ and G in combination may be

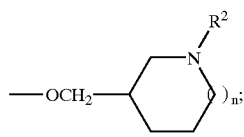

W is
(a) —CH₂—;
(b) —CH=CH—;
(c) —O—;
(d) —NR²—;
(e) —S(O)ₙ—;

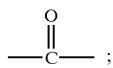
(f)

(g) —CR²(OH)—;
(h) —CONR²—;
(i) —NR²CO—;

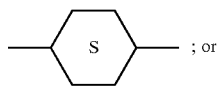
(j)

(k) —C≡C—;
R is hydrogen or C₁–C₆ alkyl;
R² and R³ are independently
(a) hydrogen; or
(b) C₁–C₄ alkyl;
R⁴ is
(a) hydrogen;
(b) halogen;
(c) C₁–C₆ alkyl;
(d) C₁–C₄ alkoxy;
(e) C₁–C₄ acyloxy;
(f) C₁–C₄ alkylthio;
(g) C₁–C₄ alkylsulfinyl;
(h) C₁–C₄ alkylsulfonyl;
(i) hydroxy (C₁–C₄)alkyl;
(j) aryl (C₁–C₄)alkyl;
(k) —CO₂H;
(l) —CN;
(m) —CONHOR;
(n) —SO₂NHR;
(o) —NH₂;
(p) C₁–C₄ alkylamino;
(q) C₁–C₄ dialkylamino;
(r) —NHSO₂R;
(s) —NO₂;
(t) -aryl; or
(u) —OH;
R⁵ and R⁶ are independently C₁–C₈ alkyl or together form a C₃–C₁₀ carbocyclic ring;
R⁷ and R⁸ are independently
(a) phenyl;
(b) a C₃–C₁₀ carbocyclic ring, saturated or unsaturated;
(c) a C₃–C₁₀ heterocyclic ring containing up to two heteroatoms, selected from —O—, —N— and —S—;
(d) H;
(e) C₁–C₆ alkyl; or
(f) form a 3 to 8 membered nitrogen containing ring with R⁵ or R⁶;
R⁷ and R⁸ in either linear or ring form may optionally be substituted with up to three substituents independently selected from C₁–C₆ alkyl, halogen, alkoxy, hydroxy and carboxy;
a ring formed by R⁷ and R⁸ may be optionally fused to a phenyl ring;
e is 0, 1 or 2;
m is 1, 2 or 3;
n is 0, 1 or 2;
p is 0, 1, 2 or 3;
q is 0, 1, 2 or 3;
or an optical or geometric isomer thereof; or a pharmaceutically acceptable salt, N-oxide, ester, quaternary ammonium salt or prodrug thereof.

In another preferred embodiment of the kits, the estrogen agonist/antagonist is a compound of formula (IA):

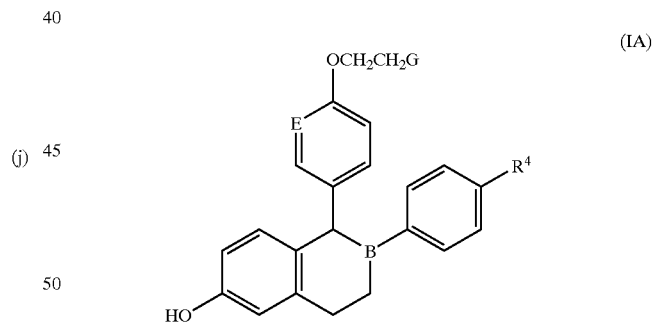
(IA)

wherein G is

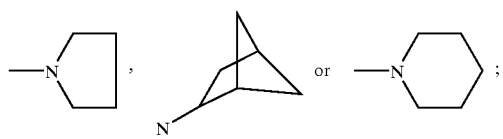

R⁴ is H, OH, F, or Cl; and B and E are independently selected from CH and N or an optical or geometric isomer thereof; or a pharmaceutically acceptable salt, N-oxide, ester, quaternary ammonium salt, or a prodrug thereof.

In another preferred embodiment of the kits, the estrogen agonist/antagonist is (−)-cis-6-phenyl-5-[4-(2-pyrrolidin-1- yl-ethoxy)-phenyl]-5,6,7,8-tetrahydro-naphthalene-2-ol or an optical or geometric isomer thereof; or a pharmaceutically acceptable salt, N-oxide, ester, quaternary ammonium salt, or a prodrug thereof.

In another preferred embodiment of the kits, the estrogen agonist/antagonist is (−)-cis-6-phenyl-5-[4-(2-pyrrolidin-1-yl-ethoxy)-phenyl]-5,6,7,8-tetrahydro-naphthalene-2-ol, D-tartrate salt.

In another preferred embodiment of the kits, the estrogen agonist/antagonist is 4-hydroxy tamoxifen, droloxifene, toremifene, centchroman, idoxifene, raloxifene, 6-(4-hydroxy-phenyl)-5-[4-(2-piperidin-1-yl-ethoxy)-benzyl]-naphthalen-2-ol, {4-[2-(2-aza-bicyclo[2.2.1]hept-2-yl)-ethoxy]-phenyl}-[6-hydroxy-2-(4-hydroxy-phenyl)-benzol[b]thiophen-3-yl]-methanone, EM-652, EM-800, GW 5638, GW 7604, or an optical or geometric isomer thereof; pharmaceutically acceptable salt, N-oxide, ester, quaternary ammonium salt, or prodrug thereof.

In another preferred embodiment of the kits, the estrogen agonist/antagonist is a compound of formula V or VI:

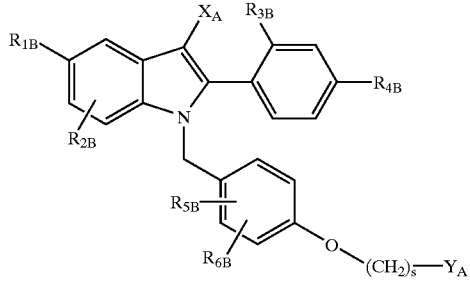

(V)

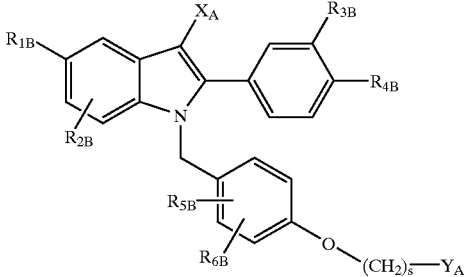

(VI)

wherein:

$R_{1B}$ is selected from H, OH, —O—C(O)—$C_1$–$C_{12}$ alkyl (straight chain or branched), —O—$C_1$–$C_{12}$ alkyl (straight chain or branched or cyclic), or halogens or $C_1$–$C_4$ halogenated ethers;

$R_{2B}$, $R_{3B}$, $R_{4B}$, $R_{5B}$, and $R_{6B}$ are independently selected from H, OH, —O—C(O)—$C_1$–$C_{12}$ (straight chain or branched), —O—$C_1$–$C_{12}$ (straight chain or branched or cyclic), halogens, or $C_1$–$C_4$ halogenated ethers, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$ is the moiety:

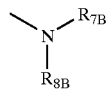

wherein:
a) $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$; or
b) $R_{7B}$ and $R_{8B}$ are concatenated to form a five-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or
c) $R_{7B}$ and $R_{8B}$ are concatenated to form a six-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or
d) $R_{7B}$ and $R_{8B}$ are concatenated to form a seven-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or
e) $R_{7B}$ and $R_{8B}$ are concatenated to form an eight-membered saturated heterocycle containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$)alkyl; or
f) $R_{7B}$ and $R_{8B}$ are concatenated to form a saturated bicyclic heterocycle containing from 6–12 carbon atoms either bridged or fused and containing one nitrogen heteroatom, the heterocycle being optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, —NH($C_1$–$C_4$ alkyl), —N($C_1$–$C_4$ alkyl)$_2$, —$NHSO_2R_{1B}$, —$NHCOR_{1B}$, —$NO_2$, or phenyl optionally substituted with 1–3 ($C_1$–$C_4$) alkyl; or an optical or geometric isomer thereof; or a pharmaceutically acceptable salt, N-oxide, ester, quaternary ammonium salt or prodrug thereof.

In another preferred embodiment of the kits, the estrogen agonist/antagonist is the compound of formula Va (TSE-424) below:

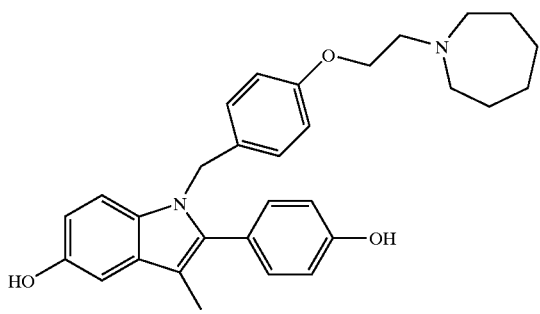

(Va)

or an optical or geometric isomer thereof; or a pharmaceutically acceptable salt, N-oxide, ester, quaternary ammonium salt or prodrug thereof.

In another preferred embodiment of the kits, the estrogen agonist/antagonist is the compound of formula III (EM-652) or formula IV (EM-800) below:

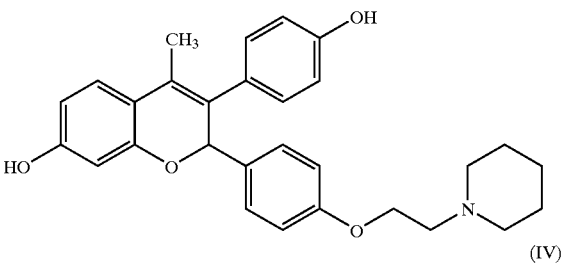

(III)

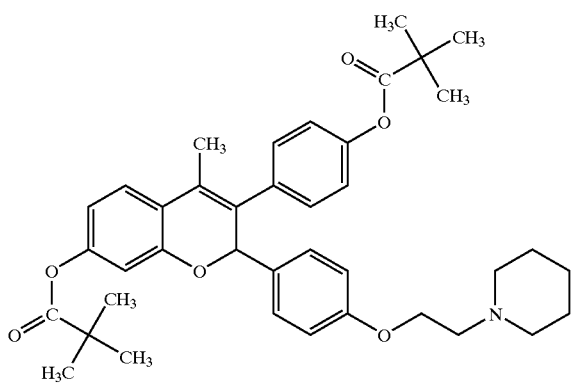

(IV)

or an optical or geometric isomer thereof; or a pharmaceutically acceptable salt, N-oxide, ester, quaternary ammonium salt or prodrug thereof.

In another preferred embodiment of the kits, the kits further comprise an additional compound that is useful to treat cancer of the liver, ovarian cancer, a desmoid tumor, glioma, pancreatic cancer, or renal cell carcinoma.

DETAILED DESCRIPTION OF THE INVENTION

The present invention provides methods of treating cancer of the liver, ovarian cancer, a desmoid tumor, glioma, pancreatic cancer, or renal cell carcinoma, the methods comprising the step of administering to a patient having cancer of the liver, ovarian cancer, a desmoid tumor, glioma, pancreatic cancer, or renal cell carcinoma a therapeutically effective amount of an estrogen agonist/antagonist. Also provided are kits for the treatment of cancer of the liver, ovarian cancer, a desmoid tumor, glioma, pancreatic cancer, or renal cell carcinoma, which kits comprise a pharmaceutical composition that contains an estrogen agonist/antagonist and instructions describing methods of using the pharmaceutical composition to treat cancer of the liver, ovarian cancer, a desmoid tumor, glioma, pancreatic cancer, or renal cell carcinoma.

The terms "treat", "treatment", and "treating" include preventative (e.g., prophylactic) and palliative treatment or the act of providing preventative or palliative treatment.

The term "patient" means animals, particularly mammals. Preferred patients are humans.

An "estrogen agonist/antagonist" is a compound that affects some of the same receptors that estrogen does, but not all, and in some instances, it antagonizes or blocks estrogen. It is also known as a "selective estrogen receptor modulator" (SERM). Estrogen agonists/antagonists may also be referred to as antiestrogens although they have some estrogenic activity at some estrogen receptors. Estrogen agonists/antagonists are therefore not what are commonly referred to as "pure antiestrogens". Antiestrogens that can also act as agonists are referred to as Type I antiestrogens. Type I antiestrogens activate the estrogen receptor to bind tightly in the nucleus for a prolonged time, but with impaired receptor replenishment (Clark, et al., Steroids 1973;22:707, Capony et al., Mol Cell Endocrinol, 1975;3:233).

"A therapeutically effective amount" is an amount of an estrogen agonist/antagonist that when administered to a patient having cancer of the liver, ovarian cancer, a desmoid tumor, glioma, pancreatic cancer, or renal cell carcinoma provides for the treatment of one or more conditions or symptoms of the cancer. Preferably, tumor size is decreased upon administration of an estrogen agonist/antagonist.

The estrogen agonists/antagonists of the invention may be administered systemically or locally. For systemic use, the estrogen agonists/antagonists herein are formulated for parenteral (e.g., intravenous, subcutaneous, intramuscular, intraperitoneal, intranasal or transdermal) or enteral (e.g., oral or rectal) delivery according to conventional methods. Intravenous administration can be by a series of injections or by continuous infusion over an extended period. Administration by injection or other routes of discretely spaced administration can be performed at intervals ranging from weekly to once to three or more times daily.

Preferred estrogen agonists/antagonists of the present invention include the compounds described in U.S. Pat. No. 5,552,412. Those compounds are described by the formula designated herein as formula (I) given below:

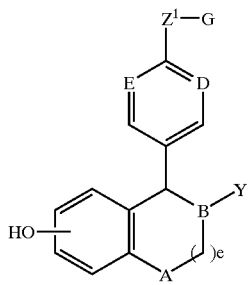

(I)

wherein:
A is selected from CH$_2$ and NR;
B, D and E are independently selected from CH and N;
Y is
  (a) phenyl, optionally substituted with 1–3 substituents independently selected from R$^4$;
  (b) naphthyl, optionally substituted with 1–3 substituents independently selected from R$^4$;
  (c) C$_3$–C$_8$ cycloalkyl, optionally substituted with 1–2 substituents independently selected from R$^4$;
  (d) C$_3$–C$_8$ cycloalkenyl, optionally substituted with 1–2 substituents independently selected from R$^4$;
  (e) a five membered heterocycle containing up to two heteroatoms selected from the group consisting of —O—, —NR$^2$— and —S(O)$_n$—, optionally substituted with 1–3 substituents independently selected from R$^4$;
  (f) a six membered heterocycle containing up to two heteroatoms selected from the group consisting of —O—, —NR$^2$— and —S(O)$_n$— optionally substituted with 1–3 substituents independently selected from R$^4$; or
  (g) a bicyclic ring system consisting of a five or six membered heterocyclic ring fused to a phenyl ring, said heterocyclic ring containing up to two heteroatoms selected from the group consisting of —O—, —NR$^2$— and —S(O)$_n$—, optionally substituted with 1–3 substituents independently selected from R$^4$;
Z$^1$ is
  (a) —(CH$_2$)$_p$W(CH$_2$)$_q$—;
  (b) —O(CH$_2$)$_p$CR$^5$R$^6$—;
  (c) —O(CH$_2$)$_p$W(CH$_2$)$_q$—;
  (d) —OCHR$^2$CHR$^3$—; or
  (e) —SCHR$^2$CHR$^3$—;
G is
  (a) —NR$^7$R$^8$;

(b) 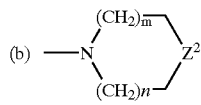

wherein n is 0, 1 or 2; m is 1, 2 or 3; Z$^2$ is —NH—, —O—, —S—, or —CH$_2$—; optionally fused on adjacent carbon atoms with one or two phenyl rings and, optionally independently substituted on carbon with one to three substituents and, optionally, independently on nitrogen with a chemically suitable substituent selected from R$^4$; or
  (c) a bicyclic amine containing five to twelve carbon atoms, either bridged or fused and optionally substituted with 1–3 substituents independently selected from R$^4$; or Z$^1$ and G in combination may be

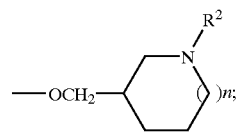

W is
  (a) —CH$_2$—;
  (b) —CH=CH—;
  (c) —O—;
  (d) —NR$^2$—;
  (e) —S(O)$_n$—;

(f) 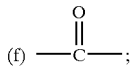

(g) —CR$^2$(OH)—;
  (h) —CONR$^2$—;
  (i) —NR$^2$CO—;

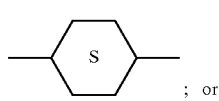 (j)

; or (k) —C≡C—;
R is hydrogen or C$_1$–C$_6$ alkyl;
R$^2$ and R$^3$ are independently
  (a) hydrogen; or
  (b) C$_1$–C$_4$ alkyl;
R$^4$ is
  (a) hydrogen;
  (b) halogen;
  (c) C$_1$–C$_6$ alkyl;
  (d) C$_1$–C$_4$ alkoxy;
  (e) C$_1$–C$_4$ acyloxy;
  (f) C$_1$–C$_4$ alkylthio;
  (g) C$_1$–C$_4$ alkylsulfinyl;
  (h) C$_1$–C$_4$ alkylsulfonyl;
  (i) hydroxy (C$_1$–C$_4$)alkyl;
  (j) aryl (C$_1$–C$_4$)alkyl;
  (k) —CO$_2$H;
  (l) —CN;
  (m) —CONHOR;
  (n) —SO$_2$NHR;
  (o) —NH$_2$;
  (p) C$_1$–C$_4$ alkylamino;
  (q) C$_1$–C$_4$ dialkylamino;
  (r) —NHSO$_2$R;
  (s) —NO$_2$;
  (t) -aryl; or
  (u) —OH;
R$^5$ and R$^6$ are independently C$_1$–C$_8$ alkyl or together form a C$_3$–C$_{10}$ carbocyclic ring;
R$^7$ and R$^8$ are independently
  (a) phenyl;
  (b) a C$_3$–C$_{10}$ carbocyclic ring, saturated or unsaturated;
  (c) a C$_3$–C$_{10}$ heterocyclic ring containing up to two heteroatoms, selected from —O—, —N— and —S—;
  (d) H;
  (e) C$_1$–C$_6$ alkyl; or (f) form a 3 to 8 membered nitrogen containing ring with R⁵ or R⁶;

R⁷ and R⁸ in either linear or ring form may optionally be substituted with up to three substituents independently selected from $C_1$–$C_6$ alkyl, halogen, alkoxy, hydroxy and carboxy;

a ring formed by R⁷ and R⁸ may be optionally fused to a phenyl ring;

e is 0, 1 or 2;

m is 1, 2 or 3;

n is 0, 1 or 2;

p is 0, 1, 2 or 3;

q is 0, 1, 2 or 3;

and optical and geometric isomers thereof; and nontoxic pharmaceutically acceptable acid addition salts, N-oxides, esters, quaternary ammonium salts and prodrugs thereof.

Additional preferred compounds are disclosed in U.S. Pat. No. 5,552,412 and are described by the formula designated herein as formula (IA):

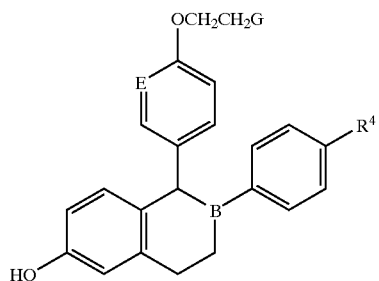

(IA)

wherein G is

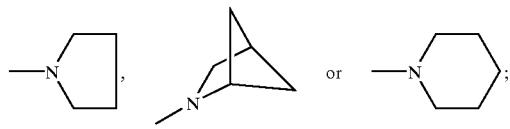

R⁴ is H, OH, F, or Cl; and B and E are independently selected from CH and N, and optical and geometric isomers thereof; and nontoxic pharmaceutically acceptable acid addition salts, N-oxides, esters, quaternary ammonium salts and prodrugs thereof.

Especially preferred compounds for the methods and kits of the invention are:

cis-6-(4-fluoro-phenyl)-5-[4-(2-piperidin-1-yl-ethoxy)-phenyl]-5,6,7,8-tetrahydro-naphthalene-2-ol;

(−)-cis-6-phenyl-5-[4-(2-pyrrolidin-1-yl-ethoxy)-phenyl]-5,6,7,8-tetrahydro-naphthalene-2-ol;

cis-6-phenyl-5-[4-(2-pyrrolidin-1-yl-ethoxy)-phenyl]-5,6,7,8-tetrahydro-naphthalene-2-ol;

cis-1-[6'-pyrrolidinoethoxy-3'-pyridyl]-2-phenyl-6-hydroxy-1,2,3,4-tetrahydronaphthalene;

1-(4'-pyrrolidinoethoxyphenyl)-2-(4''-fluorophenyl)-6-hydroxy-1,2,3,4-tetrahydroisoquinoline;

cis-6-(4-hydroxyphenyl)-5-[4-(2-piperidin-1-yl-ethoxy)-phenyl]-5,6,7,8-tetrahydro-naphthalene-2-ol;

1-(4'-pyrrolidinoethoxyphenyl)-2-phenyl-6-hydroxy-1,2,3,4-tetrahydroisoquinoline and pharmaceutically acceptable salts thereof.

An especially preferred salt of (−)-cis-6-phenyl-5-[4-(2-pyrrolidin-1-yl-ethoxy)-phenyl]-5,6,7,8-tetrahydro-naphthalene-2-ol is the D-tartrate salt.

Other preferred estrogen agonists/antagonists are disclosed in U.S. Pat. No. 5,047,431. The structure of these compounds are described by the formula designated herein as formula (II) below:

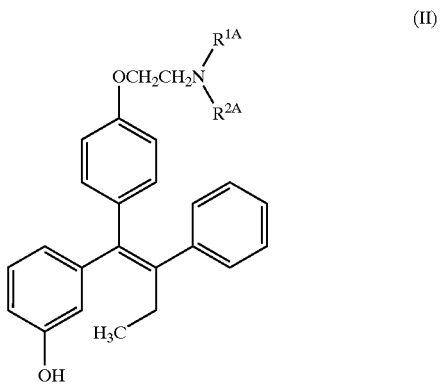

(II)

wherein $R^{1A}$ and $R^{2A}$ may be the same or different and are either H, methyl, ethyl or a benzyl group; and optical or geometric isomers thereof; and pharmaceutically acceptable salts, N-oxides, esters, quaternary ammonium salts, and prodrugs thereof. A preferred compound is droloxifene.

Additional preferred estrogen agonists/antagonists are the compounds disclosed in U.S. Pat. No. 4,536,516; 4-hydroxy tamoxifen (i.e., tamoxifen wherein the 2-phenyl moiety has a hydroxy group at the 4 position) and other compounds as disclosed in U.S. Pat. No. 4,623,660; raloxifene: (methanone, [6-hydroxy-2-(4-hydroxyphenyl)benzo[b]thien-3-yl][4-[2-(1-piperidinyl)ethoxy]phenyl]-, hydrochloride) and other compounds as disclosed in U.S. Pat. Nos. 4,418,068; 5,393,763; 5,457,117; 5,478,847 and 5,641,790; toremifene: (ethanamine, 2-[4-(4-chloro-1,2-diphenyl-1-butenyl)phenoxy]-N,N-dimethyl-, (Z)—, 2-hydroxy-1,2,3-propanetricarboxylate (1:1) and other compounds as disclosed in U.S. Pat. Nos. 4,696,949 and 4,996,225; centchroman: 1-[2-[[4-(-methoxy-2,2, dimethyl-3-phenyl-chroman-4-yl)-phenoxy]-ethyl]-pyrrolidine and other compounds as disclosed in U.S. Pat. No. 3,822,287; idoxifene: pyrrolidine, 1-[-[4-[[1-(4-iodophenyl)-2-phenyl-1-butenyl]phenoxy]ethyl] and other compounds as disclosed in U.S. Pat. No. 4,839,155; 6-(4-hydroxy-phenyl)-5-[4-(2-piperidin-1-yl-ethoxy)-benzyl]-naphthalen-2-ol and other compounds as disclosed in U.S. Pat. No. 5,484,795; and {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone and other compounds as disclosed in published international patent application WO 95/10513. Other preferred compounds include GW 5638 and GW 7604, the synthesis of which is described in Willson et al., *J. Med. Chem.*, 1994;37:1550–1552.

Further preferred estrogen agonists/antagonists include EM-652 (as shown in the formula designated herein as formula (III) and EM-800 (as shown in the formula designated herein as formula (IV)). The synthesis of EM-652 and EM-800 and the activity of various enantiomers is described in Gauthier et al., *J. Med. Chem.*, 1997;40:2117–2122.

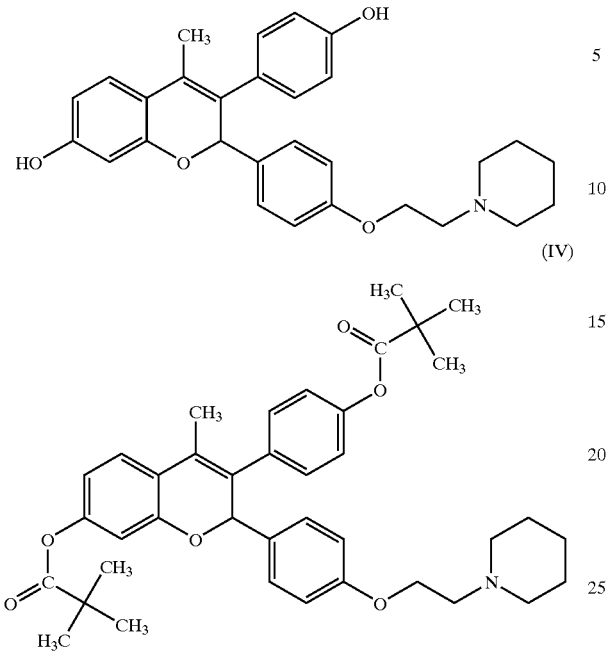

(III)

(IV)

Further preferred estrogen agonists/antagonists include TSE 424 and other compounds disclosed in U.S. Pat. Nos. 5,998,402, U.S. Pat. No. 5,985,910, U.S. Pat. No. 5,780,497, U.S. Pat. No. 5,880,137, and European Patent Application EP 0802183 A1 including the compounds described by the formulae designated herein as formulae V and VI, below:

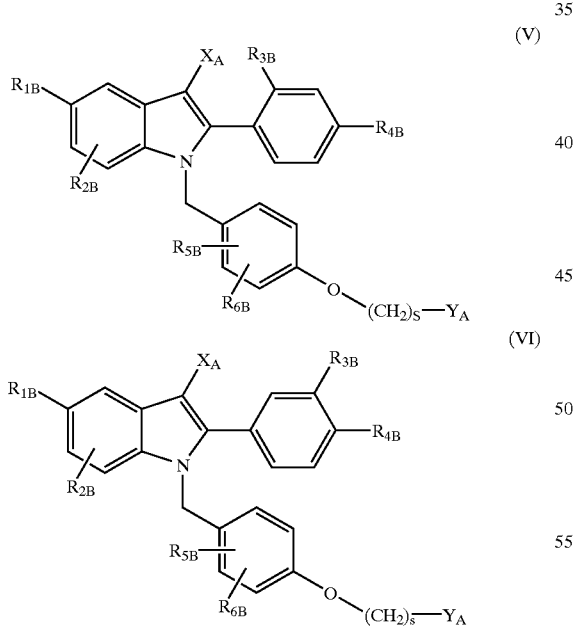

(V)

(VI)

wherein:

$R_{1B}$ is selected from H, OH or the $C_1$–$C_{12}$ esters (straight chain or branched) or $C_1$–$C_{12}$ (straight chain or branched or cyclic) alkyl ethers thereof, or halogens; or $C_1$–$C_4$ halogenated ethers including trifluoromethyl ether and trichloromethyl ether.

$R_{2B}$, $R_{3B}$, $R_{4B}$, $R_{5B}$, and $R_{6B}$ are independently selected from H, OH or the $C_1$–$C_{12}$ esters (straight chain or branched) or $C_1$–$CO_{12}$ alkyl ethers (straight chain or branched or cyclic) thereof, halogens, or $C_1$–$C_4$ halogenated ethers including trifluoromethyl ether and trichloromethyl ether, cyano, $C_1$–$C_6$ alkyl (straight chain or branched), or trifluoromethyl;

$X_A$ is selected from H, $C_1$–$C_6$ alkyl, cyano, nitro, trifluoromethyl, and halogen;

s is 2 or 3;

$Y_A$ is selected from:

a) the moiety:

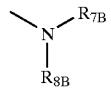

wherein $R_{7B}$ and $R_{8B}$ are independently selected from the group of H, $C_1$–$C_6$ alkyl, or phenyl optionally substituted by CN, $C_1$–$C_6$ alkyl (straight chain or branched), $C_1$–$C_6$ alkoxy (straight chain or branched), halogen, —OH, —$CF_3$, or —$OCF_3$;

b) a five-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, $C_1$–$C_4$ alkylamino, di($C_1$–$C_4$)alkylamino, —$NHSO_2R_{1B}$, —$NHCOR_{1B}$, —$NO_2$, and phenyl optionally substituted with 1–3 ($C_1$–$C_4$)alkyl;

c) a six-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_1$, —$NH_2$, $C_1$–$C_4$ alkylamino, di($C_1$–$C_4$)alkylamino, —$NHSO_2R_{1B}$, —$NHCOR_{1B}$, —$NO_2$, and phenyl optionally substituted with 1–3 ($C_1$–$C_4$)alkyl;

d) a seven-membered saturated, unsaturated or partially unsaturated heterocycle containing up to two heteroatoms selected from the group consisting of —O—, —NH—, —N($C_1$–$C_4$ alkyl)-, —N=, and —S(O)$_u$—, wherein u is an integer of from 0–2, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, —$CO_2H$, —CN, —$CONHR_{1B}$, —$NH_2$, $C_1$–$C_4$ alkylamino, di($C_1$–$C_4$)alkylamino, —$NHSO_2R_{1B}$, —$NHCOR_{1B}$, —$NO_2$, and phenyl optionally substituted with 1–3 ($C_1$–$C_4$)alkyl; or e) a bicyclic heterocycle containing from 6–12 carbon atoms either bridged or fused and containing up to two heteroatoms selected from the group consisting of —O—, —NH—, —N($C_1$-$C_4$ alkyl)-, and —S(O)$_u$—, wherein u is an integer of from 0–2, optionally substituted with 1–3 substituents independently selected from the group consisting of hydrogen, hydroxyl, halo, $C_1$-$C_4$ alkyl, trihalomethyl, $C_1$-$C_4$ alkoxy, trihalomethoxy, $C_1$-$C_4$ acyloxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$—, —CN—, —CONHR$_{1B}$—, —$NH_2$, —N=, $C_1$-$C_4$ alkylamino, di($C_1$-$C_4$) alkylamino, —NHSO$_2$R$_{1B}$, —NHCOR$_{1B}$, —NO$_2$, and phenyl optionally substituted with 1–3 ($C_1$-$C_4$) alkyl; and optical and geometric isomers thereof; and nontoxic pharmaceutically acceptable acid addition salts, N-oxides, esters, quaternary ammonium salts, and prodrugs thereof.

Preferred compounds of this invention are those having the general structures V or VI, above, wherein:

$R_{1B}$ is selected from H, OH or the $C_1$-$C_{12}$ esters or alkyl ethers thereof, and halogen;

$R_{2B}$, $R_{3B}$, $R_{4B}$, $R_{5B}$, and $R_{6B}$ are independently selected from H, OH or the $C_1$-$C_{12}$ esters or alkyl ethers thereof, halogen, cyano, $C_1$-$C_6$ alkyl, or trihalomethyl, preferably trifluoromethyl, with the proviso that, when $R_{1B}$ is H, $R_{2B}$ is not OH;

$X_A$ is selected from H, $C_1$-$C_6$ alkyl, cyano, nitro, trifluoromethyl, and halogen;

$Y_A$ is the moiety:

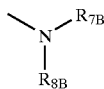

$R_{7B}$ and $R_{8B}$ are selected independently from H, $C_1$-$C_6$ alkyl, or combined by —(CH$_2$)$_w$—, wherein w is an integer of from 2 to 6, so as to form a ring, the ring being optionally substituted by up to three substituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —CONH($C_1$-$C_4$alkyl), —$NH_2$, $C_1$-$C_4$ alkylamino, $C_1$-$C_4$ dialkylamino, —NHSO$_2$($C_1$-$C_4$alkyl), —CO($C_1$-$C_4$alkyl), and —NO$_2$; and optical and geometric isomers thereof; and nontoxic pharmaceutically acceptable acid addition salts, N-oxides, esters, quaternary ammonium salts, and prodrugs thereof.

The rings formed by a concatenated $R_{7B}$ and $R_{8B}$, mentioned above, may include, but are not limited to, aziridine, azetidine, pyrrolidine, piperidine, hexamethyleneamine or heptamethyleneamine rings.

Preferred compounds of structural formulas V and VI, above, are those wherein $R_{1B}$ is OH; $R_{2B}$–$R_{6B}$ are as defined above; $X_A$ is selected from the group of Cl, NO$_2$, CN, CF$_3$, or CH$_3$; $Y_A$ is the moiety

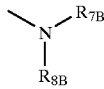

and $R_{7B}$ and $R_{8B}$ are concatenated together as —(CH$_2$)$_t$—, wherein t is an integer of from 4 to 6, to form a ring optionally substituted by up to three subsituents selected from the group of hydrogen, hydroxyl, halo, $C_1$-$C_4$ alkyl, trihalomethyl, $C_1$-$C_4$ alkoxy, trihalomethoxy, $C_1$-$C_4$ alkylthio, $C_1$-$C_4$ alkylsulfinyl, $C_1$-$C_4$ alkylsulfonyl, hydroxy ($C_1$-$C_4$)alkyl, —$CO_2H$, —CN, —CONH($C_1$-$C_4$) alkyl, —$NH_2$, $C_1$-$C_4$ alkylamino, di($C_1$-$C_4$)alkylamino, —NHSO$_2$($C_1$-$C_4$)alkyl, —NHCO($C_1$-$C_4$)alkyl, and —NO$_2$; and optical and geometric isomers thereof; and nontoxic pharmaceutically acceptable acid addition salts, N-oxides, esters, quaternary ammonium salts, and prodrugs thereof.

Another preferred compound is TSE-424 as described by the formula designated herein as formula (Va) below:

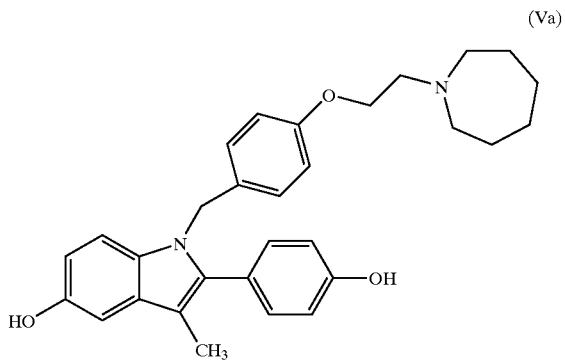

(Va)

The estrogen agonists/antagonists of this invention can be administered in the form of pharmaceutically acceptable salts. The salts are conveniently formed, as is usual in organic chemistry, by reacting the compound, when basic, with a suitable acid. The salts usually are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it. A preferred salt of (−)-cis-6-phenyl-5-[4-(2-pyrrolidin-1-yl-ethoxy)-phenyl]-5,6,7,8-tetrahydro-naphthalene-2-ol is the D-(−)-tartrate salt. It will also be recognized that it is possible to administer amorphous forms of the estrogen agonists/antagonists.

The expression "pharmaceutically acceptable salts" includes both pharmaceutically acceptable acid addition salts and pharmaceutically acceptable cationic salts. The expression "pharmaceutically acceptable cationic salts" is intended to define, but is not limited to, such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically acceptable acid addition salts" is intended to define, but is not limited to, such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

One of ordinary skill in the art will recognize that certain estrogen agonists/antagonists of this invention will contain one or more atoms which may be in a particular stereochemical, tautomeric, or geometric configuration, giving rise to stereoisomers, tautomers and configurational isomers. All such tautomers and isomers and mixtures thereof are included in this invention. Hydrates and solvates of the compounds of this invention are also included.

The subject invention also includes isotopically-labeled estrogen agonists/antagonists, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

Those of ordinary skill in the art will recognize that physiologically active compounds which have accessible hydroxy groups can be administered in the form of pharmaceutically acceptable esters. The compounds of this invention can be effectively administered as an ester, formed on the hydroxy groups. It is possible, as has long been known in pharmaceutical chemistry, to adjust the rate or duration of action of the compound by appropriate choices of ester groups.

Certain ester groups are preferred when a compound of this invention contains an ester. The estrogen agonists/antagonists including the compounds of formula I, IA, II, III, IV, V, Va, or VI may contain ester groups at various positions as defined herein above, where these groups are represented as —COOR, R is $C_1$–$C_{14}$ alkyl, $C_1$–$C_3$ chloroalkyl, $C_1$–$C_3$ fluoroalkyl, $C_5$–$C_7$ cycloalkyl, phenyl, or phenyl mono- or disubstituted with $C_1$–$C_4$ alkyl, $C_1$–$C_4$ alkoxy, hydroxy, nitro, chloro, fluoro or tri(chloro or fluoro)methyl.

The dose of a compound of this invention to be administered to a subject is rather widely variable and subject to the judgement of the attending physician. It should be noted that it may be necessary to adjust the dose of a compound when it is administered in the form of a salt, such as a laureate, the salt forming moiety of which has an appreciable molecular weight. The particular dose of a compound administered according to this invention will be determined by the circumstances including, for example, the compound administered, the route of administration, and the severity of the condition being treated.

The following dosage amounts are for an average human subject having a weight of about 65 kg to about 70 kg. The skilled practitioner will readily be able to determine the dosage amount required for a subject whose weight falls outside the 65 kg to 70 kg range, based upon the medical history of the subject. All doses set forth herein are daily doses of the free base form of the estrogen agonists/antagonists. Calculation of the dosage amount for other forms of the free base form such as salts or hydrates is easily accomplished by performing a simple ratio relative to the molecular weights of the species involved.

The general range of effective administration rates of an estrogen agonist/antagonist is from about 0.001 mg/day to about 200 mg/day. A preferred rate range is from about 0.010 mg/day to about 100 mg/day. Of course, it is often practical to administer the daily dose of compound in portions, at various hours of the day. However, in any given case, the amount of compound administered will depend on such factors as the potency of the specific estrogen agonist/antagonist, the solubility of the compound, the formulation used and the route of administration.

Methods of formulation are well known in the art and are disclosed, for example, in *Remington: The Science and Practice of Pharmacy*, Mack Publishing Company, Easton, Pa., 19th Edition (1995). Pharmaceutical compositions for use within the present invention can be in the form of sterile, non-pyrogenic liquid solutions or suspensions, coated capsules, suppositories, lyophilized powders, transdermal patches or other forms known in the art.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances that facilitate the disintegration of a tablet to release a compound when the tablet becomes wet. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavorant and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film that resists dissolution for a predictable period of time. Topical formulations may be designed to yield delayed and/or prolonged percutaneous absorption of a compound. Even the parenteral preparations may be made long-acting, by dissolving or suspending the compound in oily or emulsified vehicles which allow it to disperse only slowly in the serum.

The term "prodrug" means a compound that is transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the *A. C. S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1-C_8)$ alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl.

Similarly, if a compound of the present invention comprises an alcohol functional group, a prodrug can be formed by the replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$ alkanoyloxy) ethyl, $(C_1-C_6)$alkoxycarbonyloxymethyl, N-$(C_1-C_6)$alkoxycarbonylaminomethyl, succinoyl, $(C_1-C_6)$ alkanoyl, α-amino$(C_1-C_4)$ alkanoyl, arylacyl and α-aminoacyl, or α-aminoacyl-α-aminoacyl, where each α-aminoacyl group is independently selected from the naturally occurring L-amino acids, $P(O)(OH)_2$, $—P(O)(O (C_1-C_6)$alkyl$)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^X$-carbonyl, $R^XO$-carbonyl, $NR^XR^{X'}$-carbonyl where $R^X$ and $R^{X'}$ are each independently $(C_1-C_{10})$ alkyl, $(C_3-C_7)$cycloalkyl, benzyl, or $R_X$-carbonyl is a natural α-aminoacyl or natural α-aminoacyl-natural α-aminoacyl, $—C(OH)C(O)OY^X$ wherein $Y^X$ is H, $(C_1-C_6)$alkyl or benzyl), $—C(OY^{X0}) Y^{X1}$ wherein $Y^{X0}$ is $(C_1-C_4)$ alkyl and $Y^{X1}$ is $(C_1-C_6)$alkyl, carboxy$(C_1-C_6)$alkyl, amino$(C_1-C_4)$ alkyl or mono-N- or di-N,N-$(C_1-C_6)$alkylaminoalkyl, $—C(Y^{X2}) Y^{X3}$ wherein $Y^{X2}$ is H or methyl and $Y^{X3}$ is mono-N- or di-N,N-$(C_1-C_6)$alkylamino, morpholino, piperidin-1-yl or pyrrolidin-1-yl.

Advantageously, the present invention also provides kits for use by a consumer to treat cancer of the liver, ovarian cancer, a desmoid tumor, glioma, pancreatic cancer, or renal cell carcinoma. The kits comprise a) a pharmaceutical composition comprising an estrogen agonist/antagonist; and b) instructions describing methods of using the pharmaceutical compositions to treat cancer of the liver, ovarian cancer, a desmoid tumor, glioma, pancreatic cancer, or renal cell carcinoma.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or other health care provider, or patient, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

The kits of the present invention may also include, in addition to an estrogen agonist/antagonist, one or more additional pharmaceutically active compounds. Preferably, the additional compound is another estrogen agonist/antagonist or another compound useful to treat cancer of the liver, ovarian cancer, a desmoid tumor, glioma, pancreatic cancer, or renal cell carcinoma. The additional compound or compounds may be administered in the same dosage form as the estrogen agonist/antagonist or in different dosage forms. Likewise, the additional compounds can be administered at the same time as the estrogen agonist/antagonist or at different times.

Compounds that are used to treat cancer of the liver, ovarian cancer, a desmoid tumor, glioma, pancreatic cancer, or renal cell carcinoma and which can be used in combination with the estrogen agonists/antagonists of the present invention include 5-fluorouracil; cisplatin; paclitaxel; onconase; topotecan; hexamethylamine; ifsofamide; doxorubicin; etoposide; bleomycin; nitrosoureas such as carmustine, lomustine, procarbazine, semustine, and vincristine; methotrexate; carboplatin; actinomycin D; and streptozocin. The estrogen agonists/antagonists of the present invention can also be used in combination with radiation therapy.

All documents cited herein, including patents and patent applications, are hereby incorporated by reference.

What is claimed is:

1. A method of treating cancer of the liver, ovarian cancer, a desmoid tumor, glioma, pancreatic cancer, or renal cell carcinoma, the method comprising the step of administering to a patient having cancer of the liver, ovarian cancer, a desmoid tumor, glioma, pancreatic cancer, or renal cell carcinoma a therapeutically effective amount of a compound of formula (IA)

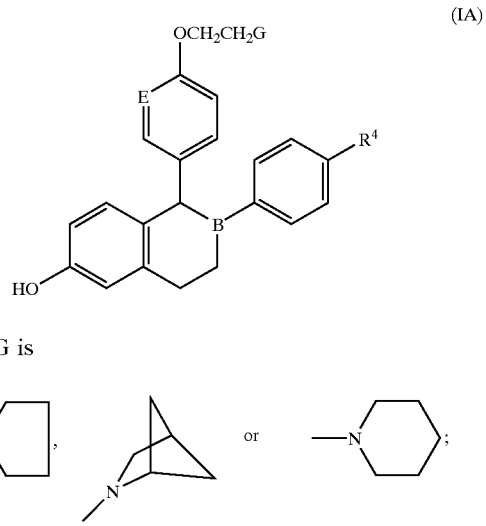

wherein G is $R^4$ is H, OH, F, or Cl; and B and E are independently selected from OH and N or an optical or geometric isomer thereof; or a pharmaceutically acceptable salt, N-oxide, ester, quaternary ammonium salt, or a prodrug thereof.

2. The method of claim 1 wherein the compound is (−)-cis-6-phenyl-5-[4-(2-pyrrolidin-1-yl-ethoxy)-phenyl]-5,6,7,8-tetrahydro-naphthalene-2-ol or an optical or geometric isomer thereof; a pharmaceutically acceptable salt, N-oxide, ester, quaternary ammonium salt, or a prodrug thereof.

3. A method of treating cancer of the liver, ovarian cancer, a desmoid tumor, glioma, pancreatic cancer, or renal cell carcinoma, the method comprising the step of administering to a patient having cancer of the liver, ovarian cancer, a desmoid tumor, glioma, pancreatic cancer, or renal cell carcinoma a therapeutically effective amount of (−)-cis-6-phenyl-5-[4-(2-pyrrolidin-1-yl-ethoxy)-phenyl]-5,6,7,8-tetrahydro- naphthalene-2-ol, D-tartrate salt.

4. The method of claim 3 wherein cancer of the liver is treated.

5. The method of claim 3 wherein ovarian cancer is treated.

6. The method of claim 3 wherein a desmoid tumor is treated.

7. The method of claim 3 wherein glioma is treated.

8. The method of claim 3 wherein pancreatic cancer is treated.

9. The method of claim 3 wherein renal cell carcinoma is treated.

* * * * *